United States Patent [19]

Sipos

[11] 4,396,599
[45] Aug. 2, 1983

[54] ANTICARIES COMPOSITION

[75] Inventor: Tibor Sipos, Lebanon, N.J.

[73] Assignee: Johnson & Johnson Products Inc., New Brunswick, N.J.

[21] Appl. No.: 303,284

[22] Filed: Sep. 17, 1981

[51] Int. Cl.³ .............................................. A61K 7/18
[52] U.S. Cl. ........................................ 424/52; 424/49
[58] Field of Search ............................................ 424/52

[56] References Cited

U.S. PATENT DOCUMENTS

| | | | |
|---|---|---|---|
| 4,022,880 | 5/1977 | Vinson et al. | 424/54 |
| 4,082,841 | 4/1978 | Pader | 424/52 |
| 4,100,269 | 7/1978 | Pader | 424/49 |
| 4,138,477 | 2/1979 | Gaffar | 424/52 |
| 4,144,323 | 3/1979 | Lambarti | 424/54 |
| 4,289,754 | 9/1981 | Dhabhar et al. | 424/52 |
| 4,289,755 | 9/1981 | Dhabhar | 424/52 |

*Primary Examiner*—Shep K. Rose
*Attorney, Agent, or Firm*—Steven P. Berman

[57] ABSTRACT

Improved protection against dental enamel caries is provided by applying to the teeth and gingivae an oral hygiene composition containing, in addition to a pharmaceutically acceptable fluoride compound, a sufficient quantity of a pharmaceutically acceptable zinc compound so that the ratio of zinc ion to fluoride ion is at least about 7:1 by weight.

13 Claims, No Drawings

ANTICARIES COMPOSITION

TECHNICAL FIELD

The present invention relates to compositions for preventing caries. More particularly, it relates to fluoride containing compositions that have enhanced activity in preventing dental enamel caries.

BACKGROUND ART

The use of soluble fluoride salts, such as stannous fluoride and sodium fluoride, to reduce the incidence of dental caries in the general population is a well known and ongoing endeavor. The administration of these fluoride compounds takes many forms, including the fluoridation of drinking water, professional treatment by dentists and incorporation in oral hygiene compositions such as dentifrices and mouthrinses.

It is also known that zinc plays a role in dental care. For example, in U.S. Pat. No. 4,160,821 issued July 10, 1979, there is disclosed a composition for treating gingivitis comprising a vehicle containing a high concentration of glycerol and a zinc salt, such as zinc chloride, that is soluble in the glycerol. In an article entitled "A Study of Zinc In Human Teeth," Arch. Oral Biol., Vol. 8, pp 135-144. 1963. Pergamon Press Ltd. (Printed in Gt. Britain), the authors, citing reports of animal studies in earlier publications by McClure (1948, Observations on induced caries in rats. J. dent. Res. 27, 34-40) and Mansell and Hendershot (1960, The spectrochemical analysis of metals in rat molar enamel, femur and incisors. Arch. oral Biol. 2, 31-37) note the relatively high level of zinc in teeth, and indicate that while the significance of the presence of zinc in teeth is uncertain and there is no evidence that zinc reduces caries in man or experimental animals, the relationship between zinc concentration in enamel and caries susceptibility should be elucidated before this element can be dismissed as a factor in dental health. An abstract of a paper entitled "Fluoride Content in Enamel After Topical Applications of $AlCl_3$, $ZnCl_2$ and NaF" presented at the 25th ORCA Congress, Caries Res. 13(2):99,1979 reports on in vitro experiments conducted on 3 groups of 10 permanent teeth each and concludes that pretreatment with $AlCl_3$ results in an appreciable increase of $F^-$ in the enamel surface but that the increase was distinctly lower in teeth treated only with NaF or pretreated with $ZnCl_2$.

In British Patent Specification No. 1,373,003, published Nov. 6, 1974, there is disclosed a dentifrice composition having activity against plaque and calculus on a tooth surface comprising a sparingly soluble zinc salt—which is defined as a zinc salt of an acid, other than zinc fluoride or its hydrates, having a water solubility greater than that of zinc phosphate and less than 1 gram of zinc per 100 ml of water at 20° C.—and a mixture of detergents. The dentifrice may also contain a compatible abrasive such as alumina and other conventional toothpaste ingredients.

U.S. Pat. No. 4,146,606, issued Mar. 27, 1979, relates to a pharmaceutical composition for dental use that can, inter alia, suppress dental caries, this composition comprising a strontium compound, a zinc compound, tannin and, optionally, a fluorine compound in such a weight proportion that the weight ratio of strontium, zinc, tannin and fluorine is 1 to 3:2 to 4:1 to 3:0 to 4.

U.S. Pat. No. 4,138,477, issued Feb. 6, 1979, discloses a composition to prevent and control mouth odor, which is also said to be effective in preventing calculus, plaque, caries and periodontal disease, containing as the essential agent a zinc-polymer complex formed by the reaction or chelation of a zinc compound with an anionic polymer containing carboxylic, sulfonic and/or phosphoric acid radicals. The composition may also include, inter alia, a fluorine-containing compound that protects the teeth against decay.

THE INVENTION

It has now been discovered that the rate of development of dental enamel caries, as characterized by proximal, smooth surface, pit and fissure caries, can be prevented or substantially retarded by the daily application to the teeth of a composition comprising a pharmaceutically acceptable oral hygiene vehicle containing an effective concentration to prevent or inhibit dental enamel caries of a pharmaceutically acceptable fluoride salt and a pharmaceutically acceptable zinc salt in sufficient amount to provide a large excess by weight of zinc ion over fluoride ion, i.e., at least about 7:1, preferably about 10:1, by weight. Furthermore, it has been found that gingival inflammation can be successfully treated or the development of gingivitis prevented with the daily application to the gingivae of the above composition.

Typical pharmaceutically acceptable fluoride compounds that are suitable for use in the compositions of this invention include sodium fluoride, potassium fluoride, lithium fluoride, aluminum fluoride, zinc fluoride, stannous fluoride, sodium monofluorophosphate, acidulated phosphate fluoride, ammonium fluoride, ammonium bifluoride and amine fluoride.

Zinc salts that are suitable for use in the compositions of this invention include zinc chloride, zinc sulfate, zinc acetate, zinc lactate, zinc salicylate, zinc thiocyanate, and, more generally, any pharmaceutically acceptable zinc salts.

As already indicated, the concentration of the zinc ion plays a significant role in the compositions of this invention. Thus, it has been found that, in order to provide anticaries activity that is a significant improvement over the activity attributable to the presence of the fluoride compound alone, the zinc ion must be present in at least about a 7-fold higher concentration by weight than that of the fluoride ion, e.g., 0.7% zinc ion and 0.1% fluoride ion. Preferably the zinc to fluoride ion ratio is at least about 8:1 or 9:1, more preferably about 10:1 by weight.

Consistent with the above ratios, the zinc ion should be present in an effective amount, while the fluoride ion concentration should be from as as low as 0.0025% up to about 3.0% by weight. The preferred range of fluoride ion concentration is about 0.005 to about 1.0% by weight, more preferably about 0.01 to about 0.5%. Similarly the zinc ion concentration should be from about 0.02 to about 25.0% by weight, preferably about 0.05 to about 8.0% by weight, more preferably about 0.1 to about 4.0% by weight. While higher concentrations of both zinc and fluoride ions could be used, no particular advantage would be afforded thereby, and there are some contraindications in the literature concerning safety of higher concentrations of fluoride and zinc ions.

Suitable pharmaceutically acceptable oral hygiene vehicles, that may be used alone or in any compatible combination, include glycerol, water, ethanol, polyethylene glycol, propylene glycol and sorbitol. Alternatively, any pharmaceutically acceptable vehicle which is compatible with the zinc and fluoride salts used may be employed.

The compositions of this invention may be in the form of a mouthwash, dentifrice, gel, powder, solution, varnish, lozenge, chewing gum, slow release device or other form suitable for oral application. Any pharmaceutically acceptable materials, such as those ordinarily used in such oral compositions, that are compatible with the zinc and fluoride ions may be employed in the compositions of this invention.

In accordance with the present invention, the compositions are applied to the teeth and the gingivae with an appliance, e.g., toothbrush, swab, impregnated dental floss or the like, on both the buccal and lingual sides, at least once daily, more preferably twice daily.

ILLUSTRATIVE EXAMPLES

The following examples will serve to illustrate typical compositions of this invention. As indicated earlier, while glycerol appears in all the illustrated compositions, this is a matter of convenience and not essential to the invention.

EXAMPLE I (SOLUTION)

| | w/w % |
|---|---|
| Glycerol, U.S.P. | 92 to 98.3 |
| Zinc fluoride | 0.02 to 0.4 |
| Zinc chloride, U.S.P. | 0.3 to 8.0 |
| Flavors | 1.0 |

The zinc salts are dissolved in glycerol with continuous stirring at 60° C.

EXAMPLES II-V (ORAL GEL)

| | II | III | IV | V |
|---|---|---|---|---|
| Glycerol, U.S.P. | 52.0 | 52.0 | 52.0 | 52.0 |
| Zinc chloride, U.S.P. | 2.0 | 0.5 | 1.0 | 3.0 |
| Sodium fluoride | 0.22 | 0.22 | 0.22 | 0.22 |
| Water | q.s. to 100 | q.s. to 100 | q.s. to 100 | q.s. to 100 |
| Pluronic F-127 (Poloxamer 407) | 18.0 | 18.0 | 18.0 | 18.0 |
| Flavors | 0.7 | 0.7 | 0.7 | 0.7 |
| Preservatives | 0.33 | 0.33 | 0.33 | 0.33 |
| Sodium saccharine | 0.5 | 0.5 | 0.5 | 0.5 |
| Color | 0.25 | 0.25 | 0.25 | 0.25 |
| | 100.0 | 100.0 | 100.0 | 100.0 | pH is adjusted to 5.5 with 0.1 N NaOH or with 0.1 N HCl.

The gel is prepared by dissolving the zinc chloride, sodium fluoride, flavor and the preservatives in glycerol. The Pluronic F-127, sodium saccharine and color are separately dissolved in water. The two solutions are blended together and left standing overnight to gel.

EXAMPLE VI (MOUTHWASH)

| | w/w % |
|---|---|
| Glycerol, U.S.P. | 10.0 to 50.00 |
| Zinc chloride, U.S.P. | 0.15 to 1.5 |
| Sodium fluoride | 0.01 to 0.22 |
| Sorbitol | 10.0 |
| Flavors | 0.5 |
| Pluronic F-108 | 2.0 |
| Preservatives | 0.3 |

-continued

| | w/w % |
|---|---|
| Color | 0.2 |
| Deionized water, q.s. to 100g | | pH is adjusted to 5.0 with 0.1 N HCl or with 0.1 N NaOH.

The zinc chloride, sodium fluoride and flavors are dissolved in glycerol. The rest of the formula ingredients are dissolved in water. The two solutions are mixed together and diluted q.s. with water.

EXAMPLE VII (TOOTHGEL)

| | |
|---|---|
| Sodium fluoride | 0.22 |
| Glycerol | 89.5 |
| Carboxymethylcellulose | 0.8 |
| Carbopol 934 | 2.0 |
| Zinc chloride, U.S.P. | 1.5 |
| Flavors | 1.0 |
| Preservatives | 0.7 |
| Deionized water | 4.28 |
| | 100.0 |

EXAMPLES VIII-XI (DENTIFRICE COMPOSITIONS)

| | VIII | IX | X | XI |
|---|---|---|---|---|
| Zinc Chloride, U.S.P. | 1.5 | 1.7 | 3.0 | 3.7 |
| Zinc Fluoride (ZnF$_2$.4H$_2$O) | — | 0.5 | — | 0.5 |
| Sodium Fluoride | 0.22 | — | 0.22 | — |
| Hydrous Silica Gel C45X | 15 | 15 | 15 | 15 |
| Sorbitol | 10.14 | 10.14 | 10.14 | 10.14 |
| Glycerin, U.S.P. | 10.30 | 10.30 | 10.30 | 10.30 |
| Titanium Dioxide | 0.5 | 0.5 | 0.5 | 0.5 |
| Pluronic F-68 | 3.0 | — | — | — |
| Natrosol 250H | 1.0 | 1.0 | 1.0 | 1.0 |
| Sodium Saccharin | 0.5 | 0.6 | 0.7 | 0.8 |
| Sodium Chloride | 0.1–1.0 | 0.1–1.0 | 0.1–1.0 | 0.1–1.0 |
| Flavor | 1.0 | 1.0 | 1.0 | 1.0 |
| Sodium Benzoate | 0.2 | 0.2 | 0.2 | 0.2 |
| Veegum K | — | 1.0 | — | — |
| Xanthan Gum | — | — | 0.5–1.5 | 0.5–1.5 |
| Myrj 52 | — | 2.0 | — | — |
| Carbomer 940 | — | — | — | 0.1–0.4 |
| Aerosil 200 | 4.0 | 4.0 | 4.0 | 4.0 |
| Purified Water, q.s. | 100.0 | 100.0 | 100.0 | 100.0 |

The pH of the final composition is adjusted to between 5.5 to 6.5, with 0.1 N HCl or 0.1 N NaOH.

EXAMPLE XII

In comparative caries studies on rats, the results of which are summarized in Table I below, the composition described in Example II was superior in reducing the development of caries over conventional fluoride containing dentifrices.

In these studies, each group consisted of thirty male Wistar rats, approximately 40 to 50 grams each, and caged by pairs in raised wire cages. At nineteen days of age the animals were weighed and randomly distributed into groups. The animals were fed diet No. 500 and provided deionized water to drink ad libitum. Approximately 0.15 g of the gel was applied with a cotton applicator per rat jaw. Treatments were administered seven days per week, twice per day, for three weeks.

Immediately prior to sacrifice all animals were observed for any visual signs of ill health and individually weighed. At the end of the three weeks, the animals were sacrificed, and the heads were then cleaned, stained, sectioned and scored by the method of Keyes. The data were tabulated and statistically analyzed for significant differences between the individual means, for both number and severity of carious lesions, by repeated-t test.

As can be seen from Table I, in two separate experiments on laboratory rats, the composition of Example II, when applied twice daily to teeth, reduce the number of carious lesions by 43% and 63% and the severity of the lesions by 45% and 68%, respectively. By contrast, a commerical dentifrice gel, containing 0.4% stannous fluoride, reduced the number of carious lesions by 18% and the severity of the lesions by 15%, under identical test conditions.

TABLE I
RAT CARIES STUDIES
The Effect of ZnCl₂ Conc. on the Development of Pit & Fissure Caries

| Formula+ | % Conc. of $ZnCl_2$ | % Conc. $Zn^{++}$ | % Conc. of NaF | % Conc. $F^-$ | % Red. in Total Lesions | % Red. in Severity of Lesions |
|---|---|---|---|---|---|---|
| B (2) | 0.5 | .24 | — | | 24* | 23* |
| C (2) | 1.0 | .48 | — | | 4 | 0 |
| A (1) | 2.0 | .96 | — | | 27* | 33* |
| D (2) | 3.0 | 1.44 | — | | 42* | 45* |
| Example III (2) | 0.5 | .24 | 0.22 | 0.1 | 10 | 8 |
| Example IV (2) | 1.0 | .48 | 0.22 | 0.1 | 10 | 7 |
| Example II (1) | 2.0 | .96 | 0.22 | 0.1 | 43* | 45* |
| Example II (3) | 2.0 | .96 | 0.22 | 0.1 | 63* | 68* |
| Example V (2) | 3.0 | 1.44 | 0.22 | 0.1 | 42* | 44* |
| E (2) | — | — | 0.22 | 0.1 | 21* | 20* |
| E (1) | — | — | 0.22 | 0.1 | 26* | 24* |
| Vehicle (2) | — | — | — | | 0 | 0 |
| Vehicle (1) | — | — | — | | 0 | 0 |
| Commercial dentifrice with 0.4% stannous fluoride | — | — | — | 0.1 | 18 | 15 |

*Significantly different, at the P < 0.05 level, from the vehicle control.
(1) Study I
(2) Study II
(3) Study III
+Formulas A–D are controls that correspond to Examples II–V, respectively, but without the NaF;
Formula E is the same basic formula as Example II, but without the ZnCl₂;
"Vehicle" is the same basic formula with both the ZnCl₂ and NaF removed.

Variation can, of course, be made without departing from the spirit and scope of the invention.

What is claimed is:

1. A composition for preventing dental enamel caries consisting essentially of a pharmaceutically acceptable oral hygiene vehicle containing an effective concentration to prevent caries of a pharmaceutically acceptable fluoride salt and a pharmaceutically acceptable zinc salt that is soluble in said vehicle, wherein the weight ratio of zinc ion to fluoride ion is at least about 10:1 and wherein the zinc salt is selected from the group consisting of zinc chloride, zinc sulfate, zinc lactate, zinc salicylate and zinc thiocyanate.

2. The composition of claim 1 wherein the fluoride ion is present in a concentration of from about 0.0025 to about 3.0% by weight.

3. The composition of claim 2 wherein the fluoride ion concentration is in the range of from about 0.005 to about 1.0%.

4. The composition of claim 2 wherein the fluoride ion concentration is in the range of from about 0.01 to about 0.5%.

5. The composition of claim 2 wherein the zinc ion is present in a concentration of from about 0.02 to about 25.0% by weight.

6. The composition of claim 5 wherein the zinc ion concentration is from about 0.05 to about 8.0%.

7. The composition of claim 6 wherein the zinc ion concentration is from about 0.1 to about 4.0%.

8. The composition of claim 1 wherein said fluoride salt is selected from the group consisting of sodium fluoride, potassium fluoride, lithium fluoride, aluminum fluoride, zinc fluoride, stannous fluoride, sodium monofluorophosphate, acidulated phosphate fluoride, ammonium fluoride, ammonium bifluoride and amine fluoride.

9. The composition of claim 1 wherein said vehicle comprises at least one member selected from the group consisting of glycerol, water, ethanol, polyethylene glycol, propylene glycol and sorbitol.

10. A method of preventing or reducing the incidence of dental enamel caries comprising applying to the teeth and gingivae of the subject to be treated a composition of claim 1.

11. The method of claim 10 wherein said composition is applied at least once daily.

12. The method of claim 11 wherein said composition is applied twice daily.

13. In the treatment of teeth to protect them against dental caries by applying thereto an effective amount of a pharmaceutically acceptable fluoride compound, the improvement which comprises applying to the teeth, concurrently with said fluoride compound, a sufficient quantity of a pharmaceutically acceptable zinc compound to provide a weight ratio of zinc ion to fluoride ion of at least about 10:1 and wherein the zinc salt is selected from the group consisting of zinc chloride, zinc sulfate, zinc lactate, zinc salicylate and zinc thiocyanate.

* * * * *